United States Patent [19]
Flom et al.

[11] Patent Number: 5,830,214
[45] Date of Patent: Nov. 3, 1998

[54] FLUID-EVACUATING ELECTROSURGICAL DEVICE

[75] Inventors: James R. Flom, Palo Alto; Matthias Vaska, Los Altos Hills; Scott Miller, Sunnyvale; Lee R. Bolduc, Mountain View, all of Calif.

[73] Assignee: Heartport, Inc., Redwood City, Calif.

[21] Appl. No.: 738,426

[22] Filed: Oct. 25, 1996

Related U.S. Application Data

[63] Continuation-in-part of Ser. No. 336,359, Nov. 8, 1994, abandoned.

[51] Int. Cl.$^6$ .................................................. A61B 17/36
[52] U.S. Cl. .............................. 606/41; 604/33; 604/35; 606/46
[58] Field of Search ........................ 606/41, 42, 45–50; 604/21, 22, 33, 35; 600/156–158

[56] References Cited

U.S. PATENT DOCUMENTS

| | | |
|---|---|---|
| 3,850,175 | 11/1974 | Iglesias . |
| 3,939,839 | 2/1976 | Curtiss . |
| 4,030,502 | 6/1977 | Iglesias . |
| 4,674,498 | 6/1987 | Stasz . |
| 4,724,836 | 2/1988 | Okada . |
| 4,802,476 | 2/1989 | Noerenberg et al. . |
| 4,850,353 | 7/1989 | Stasz et al. . |
| 4,862,890 | 9/1989 | Stasz et al. . |
| 4,903,696 | 2/1990 | Stasz et al. . |
| 4,905,691 | 3/1990 | Rydell . |
| 4,922,903 | 5/1990 | Welch et al. . |
| 4,936,281 | 6/1990 | Stasz . |
| 4,958,539 | 9/1990 | Stasz et al. . |
| 4,976,711 | 12/1990 | Parins et al. . |
| 5,007,908 | 4/1991 | Rydell . |
| 5,013,312 | 5/1991 | Parins et al. . |
| 5,026,371 | 6/1991 | Rydell et al. . |
| 5,035,696 | 7/1991 | Rydell . |
| 5,047,026 | 9/1991 | Rydell . |
| 5,047,027 | 9/1991 | Rydell . |
| 5,055,100 | 10/1991 | Olsen . |
| 5,057,107 | 10/1991 | Parins et al. . |
| 5,071,419 | 12/1991 | Rydell et al. . |

(List continued on next page.)

FOREIGN PATENT DOCUMENTS

WO 82/04216  12/1982  WIPO .

OTHER PUBLICATIONS

Valleylab, Inc., Pfizer Hospital Products Group, Laparoscopic Handswitch and Laparoscopic Handswitch Electrodes brochure, 945–600–336, Apr., 1992.
Pp. 4 and 12 of "Electrosurgical Products Hospital Catalog," Birtcher Medical Systems, Irvine, CA.
DLP FDA 510(k) Application, "IMA Electrocautery Electrode CAT #60002/60003," May 13, 1996.
DLP, Worldwide Medical Innovations product brochure, Accessory Products (Surgical), p. 46, no date.
Medtronic Surgical Products, ClearCut2 Electrosurgical Handpiece brochure, 03839 Rev B, 1995.
Valleylab, Pfizer Hospital Products Group, Electrosurgical Actives, p. 19, 945600606, Nov., 1994.
Vital Signals, Inc., Infusable Disposable Pressure Infusor Directions for Use, 0656, May, 1994.
Ximed Medical Systems, Product Label and Instructions for Use, Rev. Aug., 1990.

*Primary Examiner*—Michael Peffley
*Attorney, Agent, or Firm*—Jeffry J. Grainger; Jens E. Hoekendijk

[57] ABSTRACT

The invention provides an electrosurgical device (2) and method for cauterizing tissue and evacuating fluid from the surgical site. The device comprises an insulated conductive shaft (4) having a proximal end coupled to an electric generator (40) and a distal end coupled to an electrode (6) for cutting or coagulating tissue. The shaft has an inner lumen (14) fluidly coupled to a vacuum source (50) and a plurality of insulated side holes (8) in communication with the lumen. The side holes are configured to remain free of obstructions so that fluid, such as smoke, can be continuously evacuated during the surgical procedure.

28 Claims, 9 Drawing Sheets

U.S. PATENT DOCUMENTS

| | | |
|---|---|---|
| 5,078,717 | 1/1992 | Parins et al. . |
| 5,080,660 | 1/1992 | Buelna . |
| 5,083,565 | 1/1992 | Parins . |
| 5,084,045 | 1/1992 | Helenowski . |
| 5,085,659 | 2/1992 | Rydell . |
| 5,098,431 | 3/1992 | Rydell . |
| 5,125,928 | 6/1992 | Parins et al. . |
| 5,158,561 | 10/1992 | Rydell et al. . |
| 5,163,942 | 11/1992 | Rydell . |
| 5,171,255 | 12/1992 | Rydell . |
| 5,171,311 | 12/1992 | Rydell et al. . |
| 5,186,714 | 2/1993 | Boudreault et al. . |
| 5,192,280 | 3/1993 | Parins . |
| 5,197,963 | 3/1993 | Parins . |
| 5,197,964 | 3/1993 | Parins . |
| 5,234,428 | 8/1993 | Kaufman . |
| 5,261,905 | 11/1993 | Doresey, III . |
| 5,290,282 | 3/1994 | Casscells . |
| 5,290,286 | 3/1994 | Parins . |
| 5,300,069 | 4/1994 | Hunsberger . |
| 5,324,254 | 6/1994 | Phillips . |
| 5,342,359 | 8/1994 | Rydell . |
| 5,342,381 | 8/1994 | Tidemand . |
| 5,348,555 | 9/1994 | Zinnanti . |
| 5,352,222 | 10/1994 | Rydell . |
| 5,401,274 | 3/1995 | Kusunoki . |
| 5,413,575 | 5/1995 | Haenggi . |
| 5,445,168 | 8/1995 | Krebs . |
| 5,445,638 | 8/1995 | Rydell et al. . |
| 5,449,357 | 9/1995 | Zinnanti . |

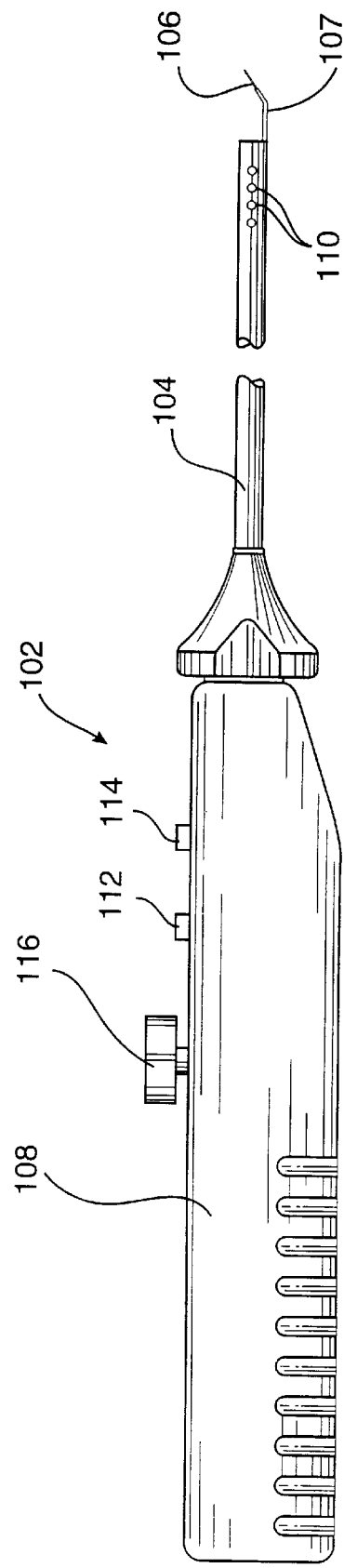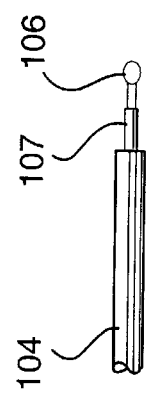
FIG. 6A
FIG. 6B

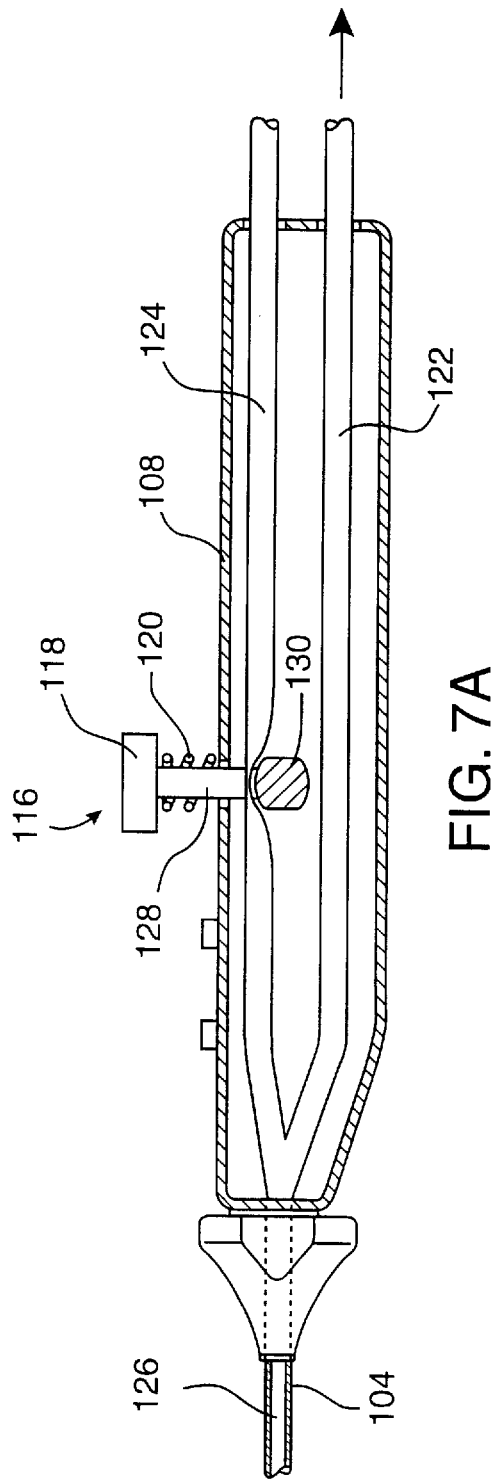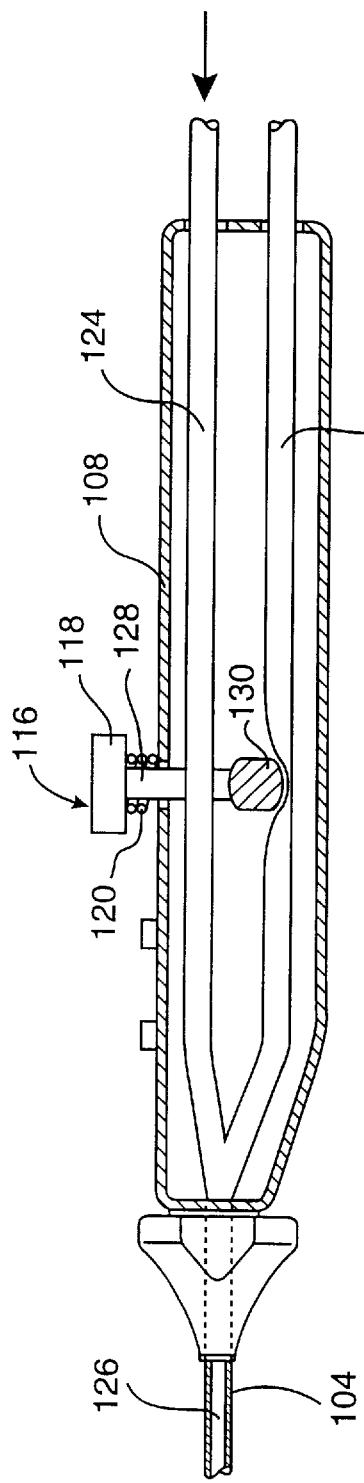

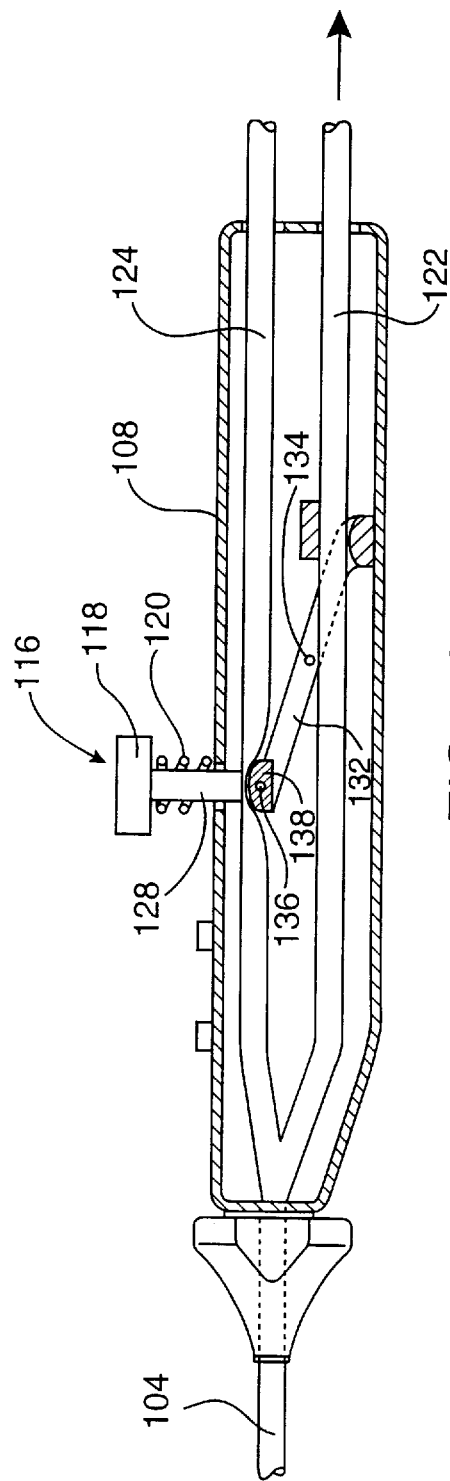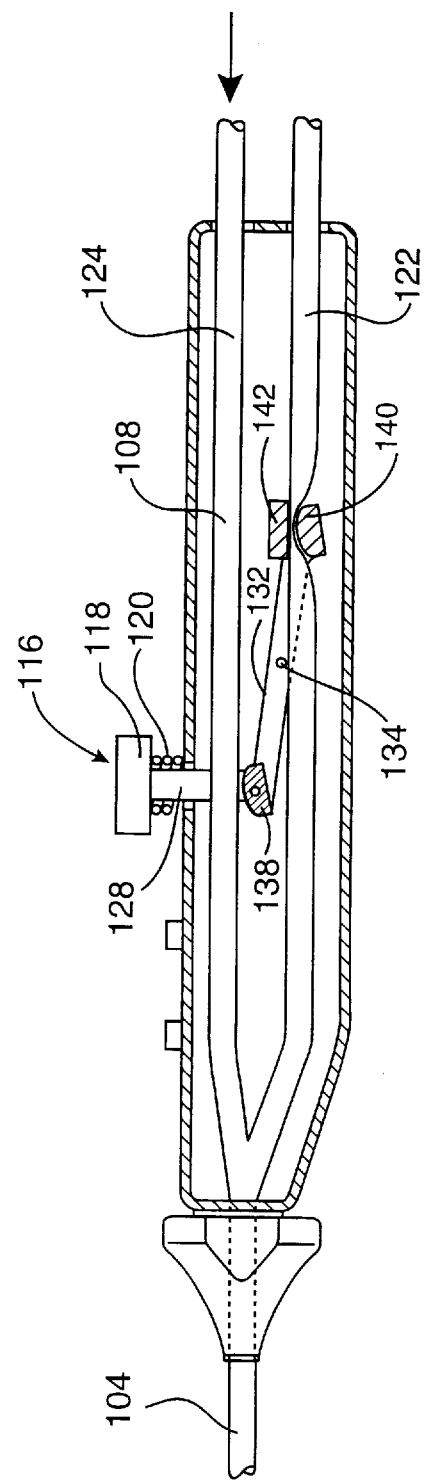

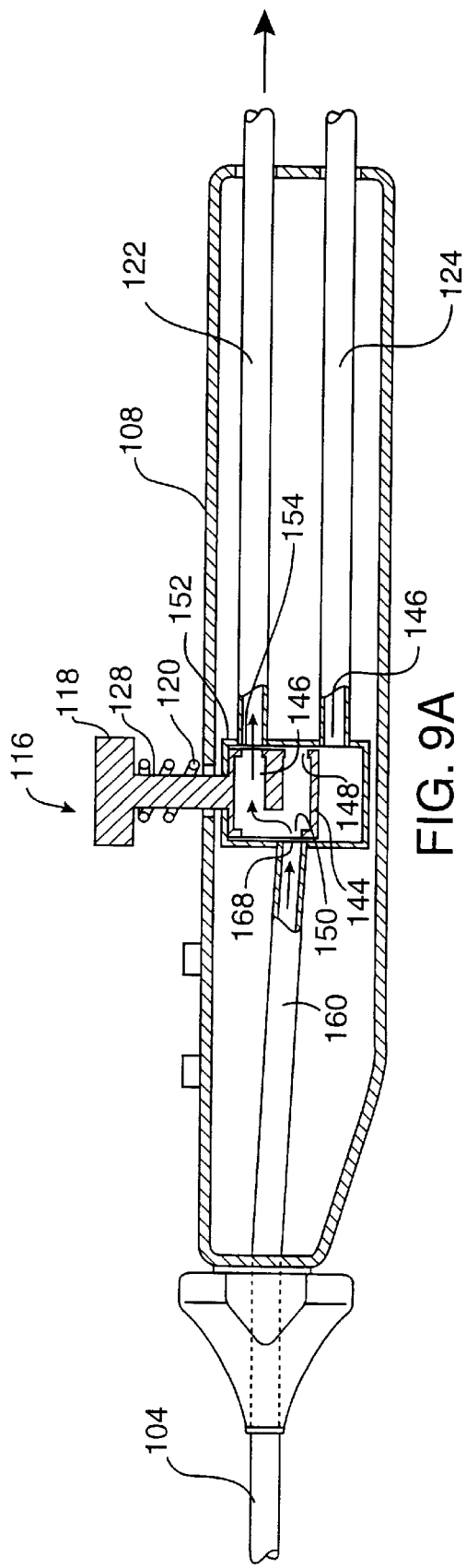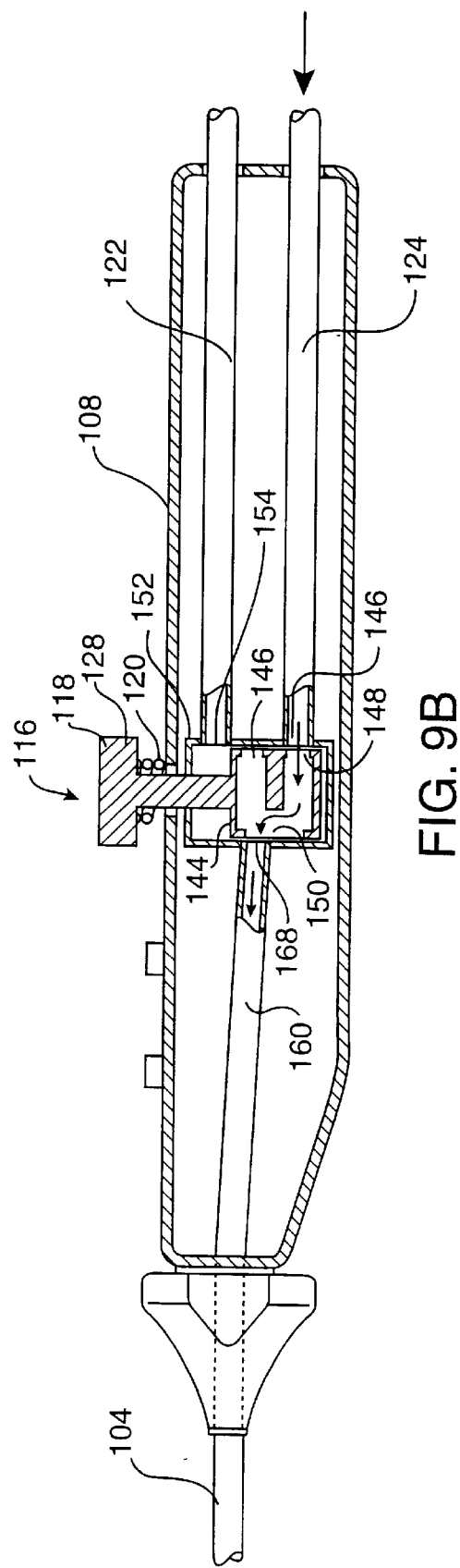
FIG. 9A
FIG. 9B

FLUID-EVACUATING ELECTROSURGICAL DEVICE

CROSS-REFERENCE TO RELATED APPLICATION

This is a continuation-in-part of application Ser. No. 08/336,359, filed Nov. 8, 1994 (now abandoned), which is incorporated herein by reference for all purposes.

FIELD OF THE INVENTION

This invention relates generally to devices for less-invasive surgical procedures, and more specifically to an electrosurgical device for cauterizing tissue and evacuating fluid from a surgical site in less-invasive surgical procedures.

BACKGROUND OF THE INVENTION

Electrosurgical devices are used for coagulating fluids and cauterizing tissue structures in various types of less-invasive surgical procedures. These devices commonly comprise a shaft having an electrosurgical electrode extending from its distal end. The electrode is connected to a source of electricity, such as a high frequency generator, for supplying a high density current to the electrode. The current at the electrode jumps across an air gap or arcs into the target tissue structure and then travels through the patient into a grounding pad or cable attached to the patient's skin. The heat generated by the current in the tissue structure causes coagulation of fluids or cauterization of tissue, depending upon the current level. In order to confine current to the electrode tip, the shaft is made of an electrically insulating material, or if conductive, the shaft is covered with an electrically insulating material such as a shrink-wrapped plastic film.

In using electrosurgical devices, whether for coagulating or cutting tissue, a large amount of smoke is generated. This smoke can obstruct or completely block the surgeons' field of vision during the operation. In addition, the smoke contains aerosolized and vaporized organic material, carbon particles and viable viral particles. These potentially infectious and/or carcinogenic materials can be inhaled by the patient or the operating team. The odor of cauterized tissue can also be irritating to the operating team.

In laparoscopic and thoracoscopic procedures, the smoke created during electrocautery can be particularly problematic. Because such procedures are carried out through small ports, trocars, or punctures in the abdominal or chest wall without making large incisions, the smoke created by electrocautery cannot easily escape from the body cavity. This can produce extremely poor visibility in the body cavity, adding further difficulty to the already challenging task of visualization in such procedures.

To solve the problems associated with the smoke produced in electrocautery, some known electrocautery devices employ suction means to withdraw from the body cavity the smoke generated at the electrode tip. In an exemplary design, a lumen extends through the shaft of the device to a distally-oriented opening at the distal end. The proximal end of the lumen is coupled to a vacuum device that sucks the smoke through the lumen and into a waste receptacle.

Known devices having smoke-evacuation capability suffer, however, from a variety of problems. When cutting tissue, the distal end of the shaft may often be pressed against the tissue, obstructing the opening in the distal end and inhibiting evacuation of smoke. Severed or loose tissue particles will often get sucked against the distal end of the tube thereby obstructing smoke evacuation through the opening. Smaller tissue particles that pass through the distal opening may clog the inner lumen further up the shaft.

What are needed, therefore, are electrosurgical devices and methods of using such devices which are adapted for cauterizing tissue and for effectively evacuating the smoke generated during cauterization. The devices and methods should be capable of continuously evacuating smoke throughout a surgical procedure without becoming clogged by tissue and other debris around the operating site. The devices should be configured for use in various surgical procedures, but should be particularly well-adapted for use in thoracoscopic and laparoscopic procedures.

SUMMARY OF THE INVENTION

The present invention provides an electrosurgical device and method of use thereof for cauterizing tissue at a surgical site and evacuating fluid from the surgical site. The device is configured to maintain a substantially open fluid path between its distal and proximal ends so that fluid, such as smoke, can be continuously evacuated throughout the procedure. The device is configured for introduction through a small percutaneous penetration in the patent, and is particularly suited for introduction through an intercostal space in thoracoscopic surgical procedures.

In one aspect of the invention, an electrocautery device comprises a shaft having proximal and distal ends, an inner lumen therebetween, and an opening at the distal end in communication with the inner lumen. An electrode is attached to the distal end of the shaft and extends distally therefrom. A handle is attached to the proximal end of the shaft, and a connector is mounted on the handle that is adapted for connection to a source of electricity. A conductor extends between the connector and the electrode for conducting electricity to the electrode for cauterizing tissue. An irrigation port is provided on the handle that is fluidly connected to the inner lumen and adapted for connection to a source of irrigation fluid. A suction port is also provided on the handle, is fluidly connected to the inner lumen and is adapted for connection to a source of suction. A switch on the handle is movable between a first position and a second position, wherein, in the first position, the irrigation port is fluidly isolated from the inner lumen and the suction port is in fluid communication with the inner lumen, and in the second position, the suction port is fluidly isolated from the inner lumen and the irrigation port is in fluid communication with the inner lumen.

In a further embodiment, the electrosurgery device has an insulated conductive shaft that has a proximal end adapted for electrically coupling the shaft to a source of electrical energy. An electrode is coupled to the distal end of the shaft through which electric current can be delivered for cauterizing tissue or coagulating fluids. The shaft has an inner lumen between the proximal and distal ends that may be fluidly coupled to a source of vacuum at the proximal end. The shaft further includes at least one insulated side hole near the distal end in fluid communication with the inner lumen. With this configuration, fluid such as smoke generated from cauterizing or coagulating can be continuously evacuated through the side hole and the inner lumen of the shaft without obstruction.

In one embodiment, the device includes a plurality of insulated side holes in the wall of the shaft near its distal end, each in communication with the inner lumen. The exterior of the shaft is covered with an electrically insulating material. The side holes have side walls also covered with the insulating material to prevent an electric arc from being generated between the side holes and the surrounding tissue. The side holes are spaced proximally from the distal end of the shaft so that fluid can be evacuated even when the distal end of the shaft is pressed against a tissue or otherwise obstructed. Preferably, the diameter of the side holes is substantially smaller than the diameter of the shaft so that smoke may pass through, but larger tissue particles may not. This inhibits large tissue particles from obstructing or blocking the lumen in the shaft. The side holes may be round, rectangular slots, ovals, or other shapes.

The device further includes switch means coupled to the proximal end of the shaft, for selectively connecting the electricity source to the shaft (and therefore the electrode). The switch means may comprise a button mounted to the proximal end of the shaft, or a foot pedal switch.

Preferably, the shaft is made of a conductive material such as stainless steel so that the shaft itself conducts electrical current from the generator to the electrode. The shaft may be tubular so that the diameter of the inner lumen is maximized to provide a large fluid passage through the inner lumen. In this way, tissue particles that are sucked into the shaft are likely to pass completely through the lumen rather than obstructing it.

In a preferred configuration, the electrode and the distal end of the shaft are configured for introduction into the thoracic cavity through a small incision or puncture in an intercostal space. The diameter of the shaft, or largest transverse dimension of the electrode, is usually less than 12 mm, and preferably about 5 mm. The electrode has a planar or large-curvature surface forming a spatula-shaped tip. This configuration allows the surgeon to see the electrode more clearly within the body cavity with conventional endoscopic visualization devices, such as an endoscope. In an exemplary embodiment, the electrode is configured for dissecting an internal mammary artery away from the inner thoracic wall to expose the mammary artery for use in a coronary artery bypass grafting procedure.

The electrocautery device is preferably constructed by selecting a tubular shaft of a biocompatible metal such as stainless steel of the appropriate length and diameter. A plurality of side holes are drilled in the wall of the shaft near the distal end. An electrode is then formed at the distal end of the shaft, usually by welding a steel tip of the desired shape to the distal end of the shaft. The shaft is then coated by a sprayed powder coating process using an electrically-insulating polymer such as polyolefin with a poly tetrafluoroethylene (PTFE) coating, so that the material coats the exterior of the shaft and the sidewalls of the side holes. The insulating material is allowed to cure or solidify, and the distal tip of the electrode is then stripped of the insulating material to expose that portion of the electrode to be used for cauterization and coagulation. Alternatively, the electrode tip may be masked during the coating process. An insulating handle may be mounted to the proximal end of the shaft, to which an electrical switch and connector may be mounted, and to which a hose barb or other fluid connector mounted for connection to a vacuum source. In an alternative process, the shaft is coated by dipping the shaft into a container of liquefied insulating material so that the exterior surface and sidewalls of the side holes are covered. The material is then allowed to solidify and cure until hard.

One advantage of spray coating the shaft with insulating material is that the coating of insulation is formed around the shaft. This coating is generally less susceptible to tearing or damage than a shrink wrapped plastic film when the shaft is introduced through a percutaneous incision or cannula. In addition, the spray coating ensures that the side walls of the side holes are insulated so that an electric current does not arc from exposed portions of the shaft on the hole side walls.

A further understanding of the nature and advantages of the invention may be realized by reference to the remaining portions of the specification and the drawings.

BRIEF DESCRIPTION OF THE DRAWINGS

FIG. 6A is a side view of an electrosurgical device according to the invention in a further embodiment thereof.

FIG. 6B is a top view of a distal end of the electrosurgical device of FIG. 6A.

FIGS. 7A–B, 8A–B, and 9A–B are side cross-sections of a handle of the electrosurgical device of FIG. 6A, illustrating various embodiments of a switch for alternating between suction and irrigation.

DESCRIPTION OF THE PREFERRED EMBODIMENT

Figure 1:
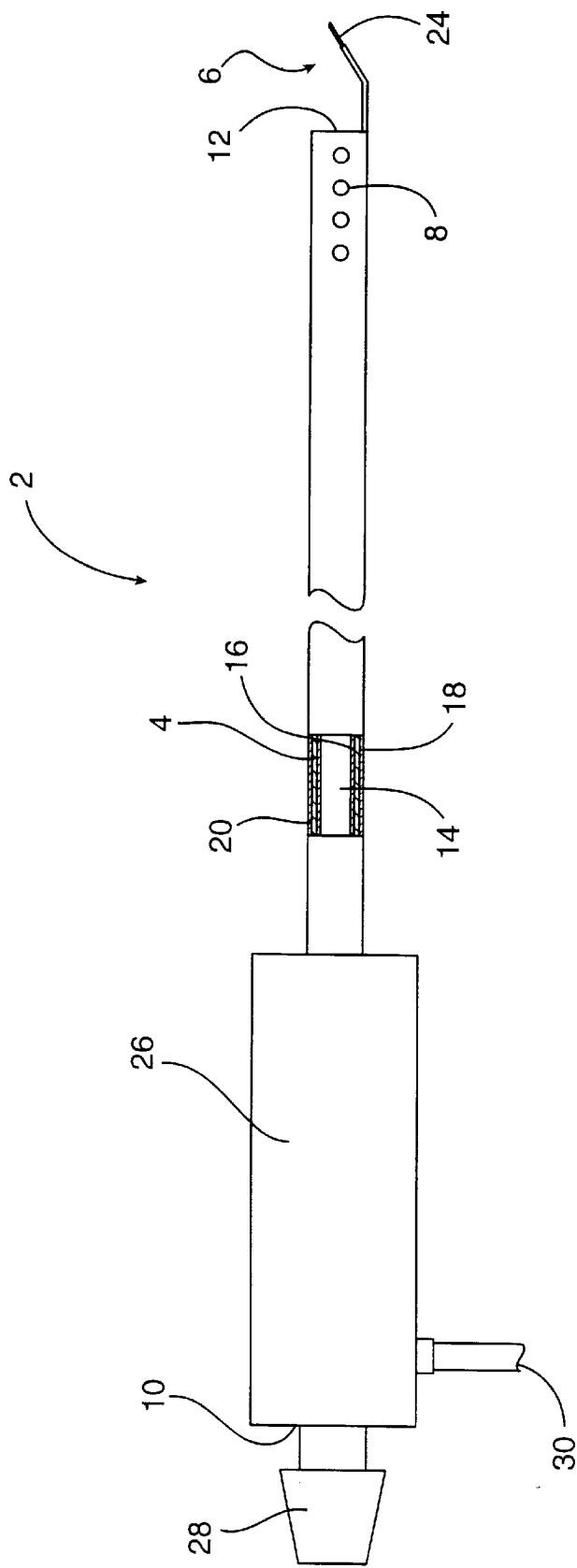
FIG. 1 is a side view of an electrosurgical device according to the principles of the present invention.

Referring to the drawings, an electrosurgical device 2 is illustrated according to the principles of the present invention. Referring to FIG. 1, electrosurgical device 2 includes an insulated shaft 4 electrically coupled to an electrode 6 and having a plurality of side holes 8 for evacuation of fluid from a surgical site.

Shaft 4 has a proximal end 10, a distal end 12 and an inner lumen 14 therebetween. Shaft 4 is preferably a stainless steel tube having an outer diameter in the range of 2–8 mm, usually 3–5 mm, so as to fit within a cannula having an internal diameter in the range of 2–10 mm. Shaft 4 can also be introduced directly through a percutaneous incision in the patient. Shaft 4 has a length of about 10–40 cm so as to reach a target site in a body cavity, and to extend sufficiently out of the body cavity to facilitate easy manipulation of electrosurgical device 2. In one embodiment, shaft 4 is configured to reach an internal mammary artery in the thoracic cavity from a left lateral position in the chest, having a length between 20 cm and 30 cm, and preferably about 25 cm.

Shaft 4 has an interior surface 16 defined by lumen 14 and an exterior side surface 18. Lumen 14 has a diameter slightly smaller than the outer diameter of shaft 4, or about 2–7 mm, depending on the shaft diameter, to provide a passage of maximum diameter for evacuation of smoke and other fluids. Exterior side surface 18 of shaft 4 is covered by a layer of electrically insulating material 20, such as Teflon or nylon, so that electric current will not arc between an exposed portion of shaft 4 and the surrounding tissue.

Electrosurgical device 2 further includes a handle 26 attached to proximal end 10 of shaft 4. Handle 26 includes a fluid connector such as a hose barb in communication with lumen 14 for coupling to either an irrigation or a vacuum source (not shown in FIG. 1). Handle 26 further includes a conventional electrical connector 30, such as a banana plug, electrically coupled to shaft 4 and adapted for attachment to a source of electrical energy, such as an electrical generator (further details of the vacuum source and generator are described below with reference to FIG. 4). Handle 26 may also include a finger switch (not shown) for selectively actuating the electrical generator or for shifting the frequency of the electric current so as to switch between coagulation and cutting. An additional switch may be provided on handle 26 for selectively actuating suction or irrigation through lumen 14.

Figure 2A:
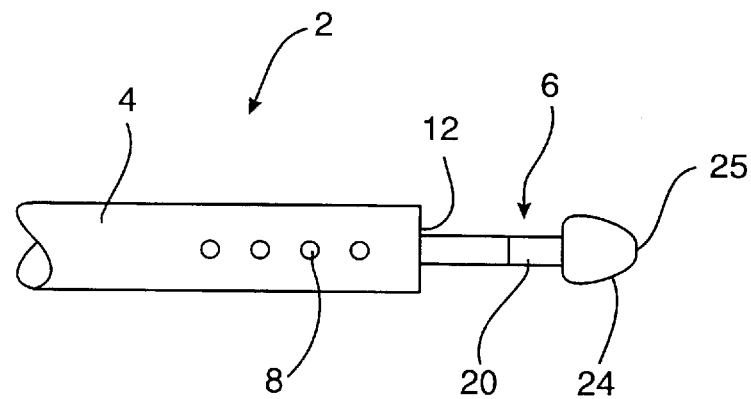
FIG. 2A is a top view of a distal end of the electrosurgical device of FIG. 1.
Figure 2B:
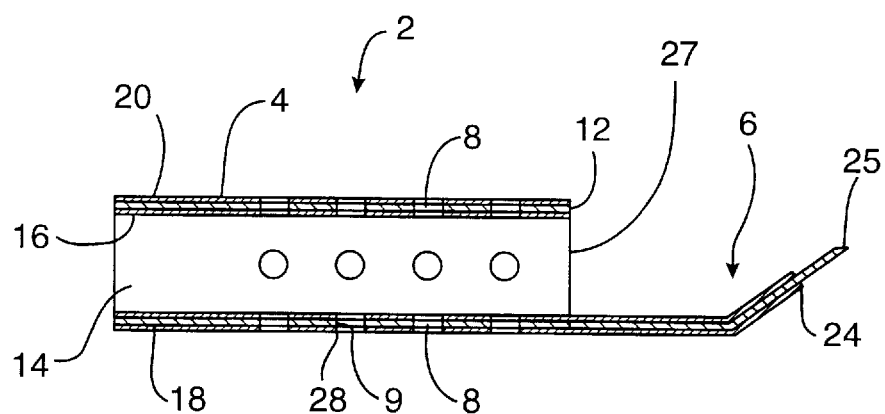
FIG. 2B is a side cross-sectional view of a distal end of the electrosurgical device of FIG. 1.

Referring to FIGS. 2A and 2B, electrode 6 extends distally from distal end 12 of shaft 4 and has a distal portion bent at an angle of between about 5° and 60°, usually about 20°, relative to the longitudinal axis of shaft 4. Electrode 6 has a wide, generally planar tip 24 forming a spatula configuration. This configuration facilitates viewing tip 24 through an endoscope in minimally invasive procedures. Preferably, tip 24 tapers inward in the distal direction to form a thin cutting surface with a curved distal end 25 for procedures that require precise incisions. Insulating material 20 covers only a portion of electrode 6 so that at least planar tip 24 is exposed for cauterizing tissue. It will be noted that the invention is not limited to the spatula-shaped electrode described above and shown in the figures. Electrode 6 can comprise any of a variety of shapes, such as a pencil tip, L-hook, J-hook, tube, cutting loop, etc. In addition, electrode 6 may be detachable by means of threads or other type of coupling mechanism, to allow interchanging electrodes of various types.

As shown in FIG. 2B, shaft 4 has a distally-oriented opening 27 in distal end 12 for the evacuation of smoke, blood, tissue particles and other debris from the surgical site. However, should distal opening 27 become obstructed or blocked during the surgical procedure, smoke can be continuously evacuated through side holes 8 disposed proximally from distal end 12, even when distal end 12 is pressed against tissue. Side holes 8 have a substantially smaller diameter than shaft 4, preferably about 0.5–2.0 mm. This effectively prevents larger tissue particles that have been severed during cauterization from blocking or obstructing side holes 8 while allowing smoke and other fluids to pass through.

Side holes 8 each have a side wall 9 covered by a layer 28 of insulating material 20 so that electric current passing through shaft 4 will not jump or arc from an exposed portion of shaft 4 on side wall 9 into the surrounding tissue. In a preferred configuration, a plurality of side holes 8, usually about sixteen in number, are positioned circumferentially around exterior side surface 18 and spaced axially along shaft 4 to enhance the evacuation of smoke and other fluids. It will, of course, be apparent to one of ordinary skill in the art that side holes 8 could have a variety of different arrangements around shaft 4, including axial, spiral, or circular configurations.

Figure 3A:
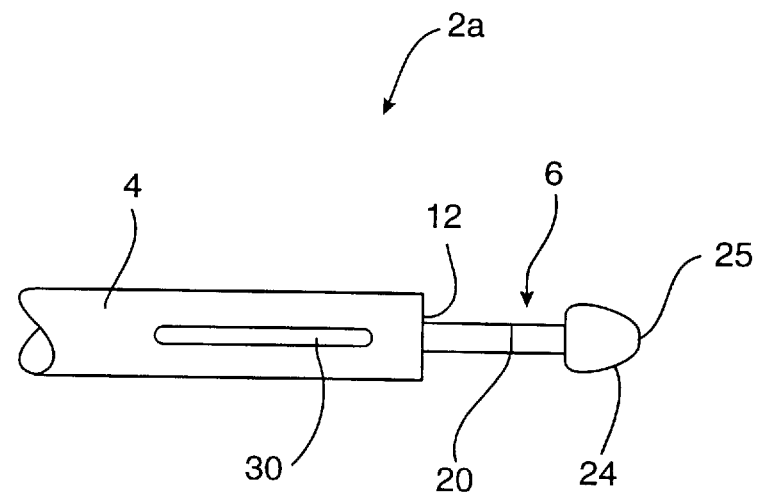
FIG. 3A is a top view of a distal end of an electrosurgical device according to the invention in an alternative embodiment.
Figure 3B:
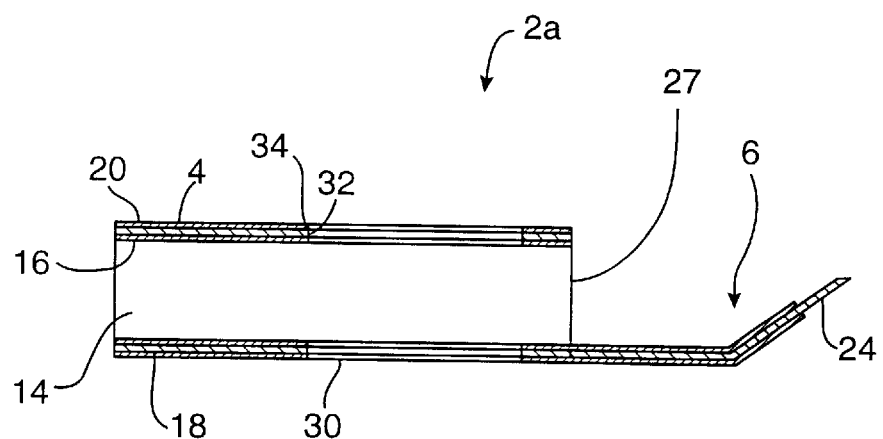
FIG. 3B is a side cross-sectional view of the distal end of the electrosurgical device of FIG. 3A.

FIGS. 3A and 3B illustrate an alternative embodiment of electrosurgical device 2a. In this embodiment, the side holes are replaced with elongated slots 30. Slots 30 generally extend in the axial direction and preferably have a small width, e.g. about 0.5–2.0 mm, to prevent tissue particles from passing through slots 30. Slots 30 preferably have a length of about 5–10 mm in the axial direction to provide a large enough opening for the continuous evacuation of smoke. As shown in FIG. 3B, slots 30 have side walls 32 that are covered by a layer 34 of insulating material 20 to ensure that shaft 4 remains completely insulated to protect the patient from electric current.

Figure 4:
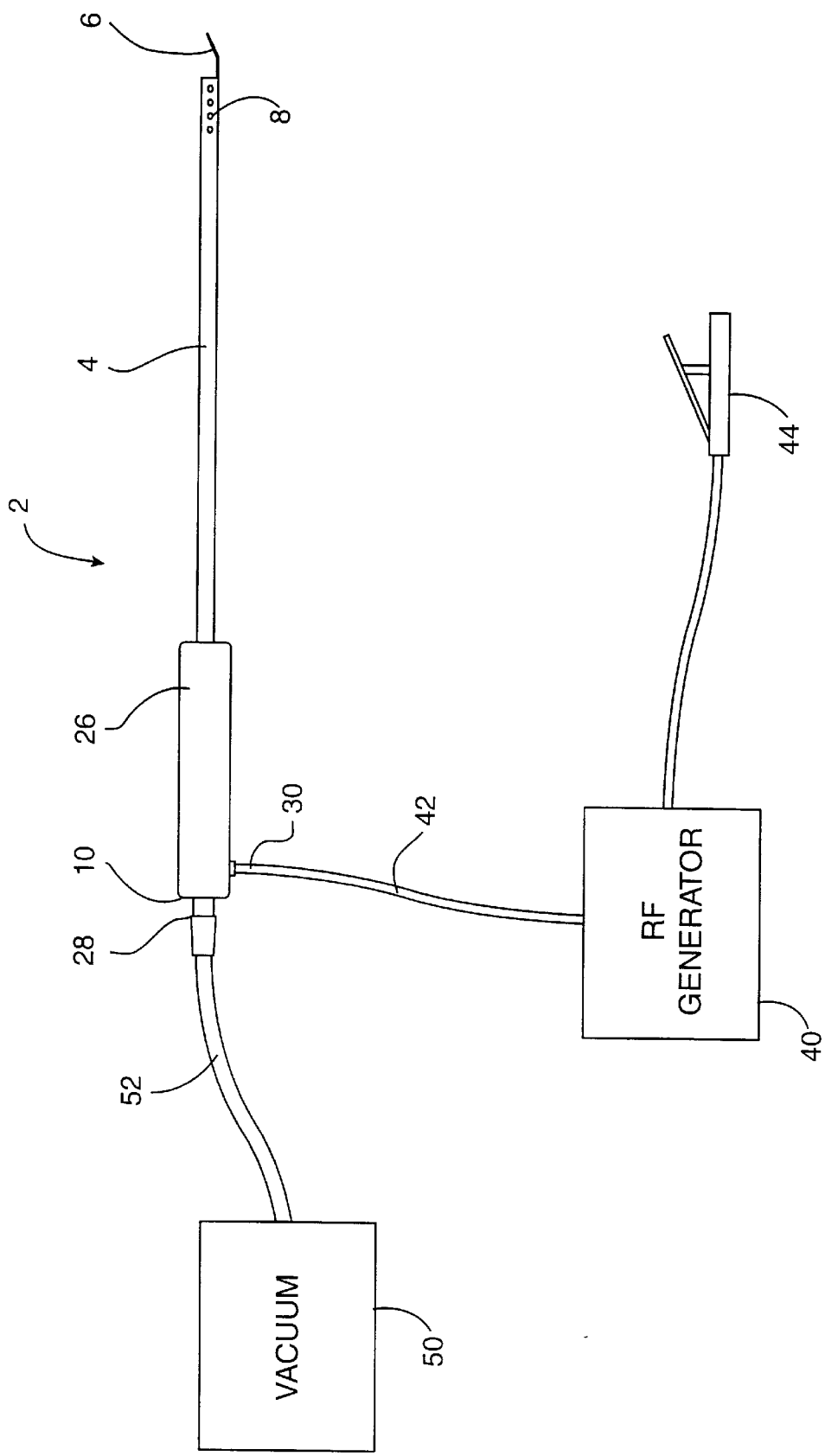
FIG. 4 is a schematic view of the electrosurgical device of FIG. 1 coupled to an electric generator and a source of vacuum.

Referring to FIG. 4, electrosurgical device 2 is coupled to a source of electrical energy such as a radio frequency generator 40 by coupling electrical connector 30 to one pole of generator 40 via an electrical line 42. A second electrode of generator 40 may be provided in the form of a large plate electrode (which may or may not be grounded) for engagement with the skin of the patient (in the case of a unipolar system). In the case of a bipolar system, any suitable bipolar electrode may be used.

In one embodiment, a foot pedal switch 44 is electrically connected to generator 42 for switching electric power to electrode 6 on and off. In another embodiment, handle 26 includes a button (not shown), coupled to electrical line 42, for actuating generator 40. A switch may also be provided for selecting the frequency of the current for either coagulating or cutting, or two separate buttons may be provided, one for coagulation and one for cutting.

As shown in FIG. 4, electrosurgical device 2 is coupled to a source of vacuum 50 by a suction line 52 attached to port 28. Preferably, vacuum source 50 is a standard vacuum canister found in most operating rooms, which effectively evacuates fluid using standard vacuum pressures and flows specified for operating rooms. Port 28 may also be attached to a source of liquid, such as saline, for irrigation of an interior portion of the patient's body. This may be useful in clearing away debris from the area at which electrode 6 is operating to provide the surgeon with relatively unobstructed visibility. Alternatively, handle 26 may include a second port for attachment to the fluid source so that both of these operations are available to the surgeon during the operation. A foot pedal or handle-mounted switch may also be provided to allow the operator to selectively actuate suction or irrigation. Either or both of these switches may be of the type which allow selectable variation of the vacuum pressure or irrigation flow rate. For example, a sliding vent on handle 26 in communication with lumen 14 would allow selectable diversion of the vacuum outside of lumen 14 to vary the strength of vacuum exerted through lumen 14. An electronic, slidable or rotatable valve on handle 26, suction line 52, or vacuum source 50 may also be used. Additionally, the vacuum switch may be electrically coupled to the electrocautery switch so that vacuum is automatically turned on when electrocautery is turned on, and turned off when electrocautery is turned off.

To manufacture electrosurgical device 2, shaft 4 is machined using conventional machining techniques. Shaft 4 is constructed out of a conductive material, preferably a biocompatible metal such as stainless steel or tungsten carbide. Side holes 8 are then drilled into shaft 4. Electrode 6 is attached to distal end 12 of shaft 4 by welding or other known technique. Electrode 6 is then masked, and shaft 4 is sprayed with an electrically insulating powdered polymer 20, such as polyolefin, to completely coat the exterior of shaft 4, sidewalls 26 of side holes 8, and at least the end portions of the inner wall of shaft 4 around lumen 14. A second layer of poly tetrafluoroethylene (PTFE) may be sprayed over or together with the polyolefin. The layer(s) of insulating material are then cured by heating shaft 4 in an oven. Handle 26 may then be mounted to the proximal end of shaft 4 by threaded connection, press-fit, set screw, adhesive bonding, or other conventional method.

In an alternative process, shaft 4 may be dipped into a container of electrically insulating liquefied polymer, such as nylon or Teflon, which leaves a thin insulating coating on all surfaces of shaft 4, including side walls 26 of side holes 8. The shaft is dipped repeatedly until a suitable thickness of the coating has adhered to shaft 4. The insulating material 20 is then solidified, preferably, by curing at room temperature.

Alternatively, a sheath (not shown) of ABS or other suitable plastic may be mounted coaxially over shaft 4. The sheath may be axially slidable relative to the shaft to allow the sheath to be extended beyond the distal end of the shaft so as to surround electrode tip 24. In this way, the sheath may be used to protect the electrode tip when not in use, and may also function as a suction tube that may be slid beyond the electrode tip to evacuate fluids from the surgical site. The sheath may include side holes in communication with the side holes in shaft 4.

The invention may be used in a variety of surgical procedures within body cavities. The invention is particularly well-adapted for dissecting an internal mammary artery away from the inner thoracic wall in a coronary artery bypass grafting procedure.

A method for preparing an internal mammary artery for a coronary artery bypass grafting procedure according to the invention will now be described in conjunction with FIG. 5. A more complete description of instruments and techniques for performing thoracoscopic coronary artery bypass grafting can be found in commonly assigned U.S. Pat. Nos. 5,452,733 and 5,501,698, which are incorporated herein by reference. The patient undergoing the procedure is placed under general anesthesia and prepared in a conventional manner for cardiac surgery. A plurality of access trocar sleeves 52, 54, 56 will be positioned in percutaneous intercostal penetrations of the patient's chest for introduction of electrosurgical device 2 and other surgical instruments. Trocar sleeves 52,54,56 will be positioned within intercostal spaces in the left lateral chest of the patient, generally within the second, third, fourth, fifth, sixth or seventh intercostal spaces. To facilitate the dissection of the mammary artery, electrosurgical device 2 will preferably be introduced through a percutaneous intercostal penetration in either the third or fourth intercostal space. Suitable trocar sleeves are available from United States Surgical Corp. of Norwalk, Conn., under the brand name "Thoracoport". Although trocar sleeves are described as the preferred method of introducing instruments into the thoracic cavity, electrosurgical device 2 can be introduced directly through a small intercostal incision in the patient's chest. Trocar sleeves are preferred, however, to provide an open passage into the thoracic cavity and to protect adjacent tissue from injury.

Figure 5:
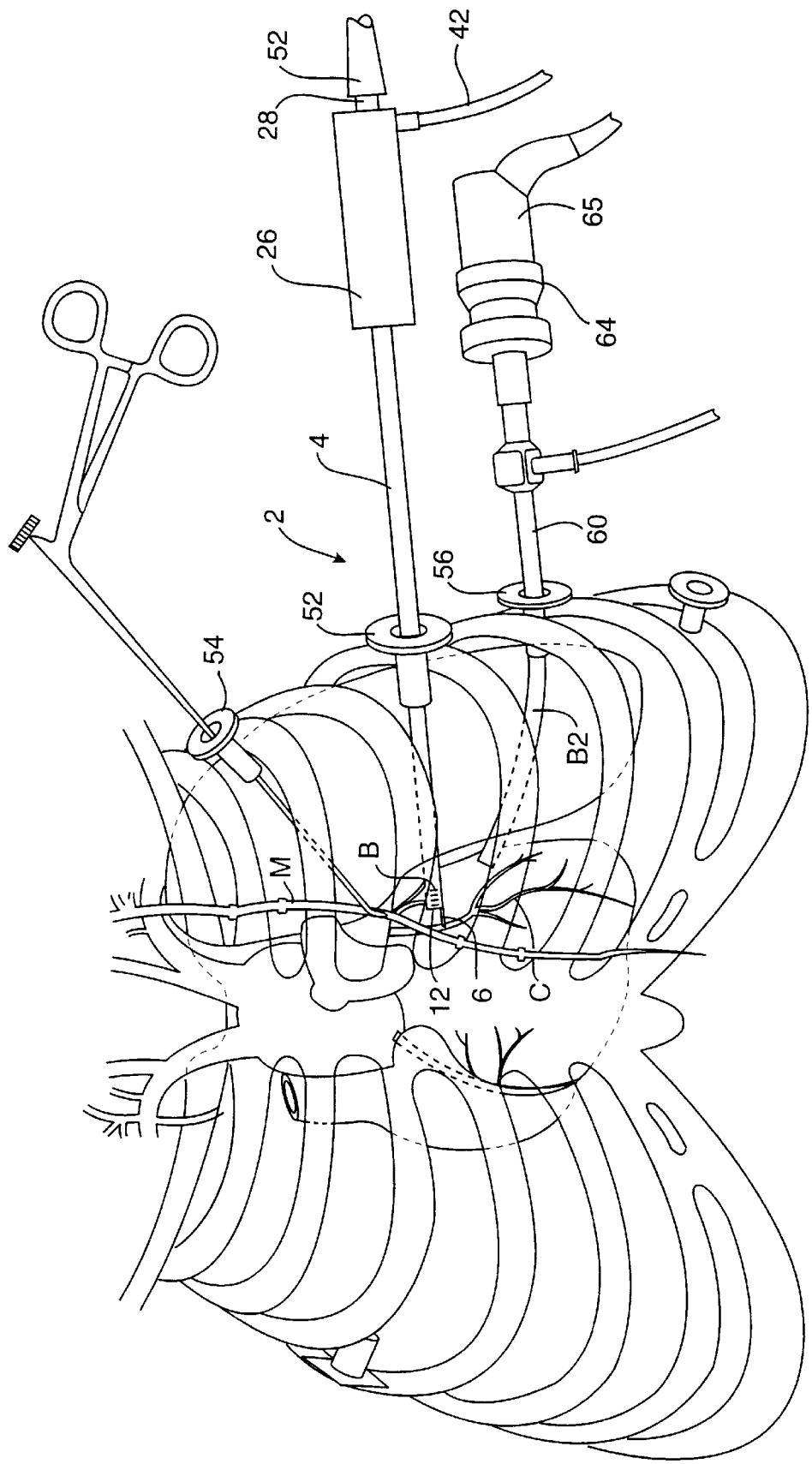
FIG. 5 is a schematic illustration showing the electrosurgical device of FIG. 1 dissecting a left mammary artery from the inner thoracic wall in a thoracoscopic coronary artery bypass grafting procedure.

The method of the invention will be described in reference to grafting the left internal mammary artery M to the left anterior descending coronary artery C, as shown in FIG. 5. Mammary artery M is located on the anterior side of the inner chest wall just lateral to the sternum. A viewing scope 60 is introduced through trocar sleeve 56 to a position suitable for viewing artery M on the inner chest wall. Viewing scope 60 can be any conventional viewing scope such as an endoscope, laparoscope, or thoracoscope, which typically consist of an elongated tube 62 containing a lens system and an eyepiece or camera mount 64 at the proximal end of the tube 62. A small video camera 65 is preferably attached to the camera mount and connected to a video monitor to provide a video image of the procedure. The viewing scope may also have an articulating tip (not shown) that can be deflected or rotated by manipulating an actuator on a proximal end of tube 62. This type of scope is commercially available from Baxter Healthcare Corp. of Deerfield, Ill.

Before the anastomosis procedure begins, the left lung will be collapsed to facilitate viewing of the operation. A double lumen endotracheal tube may be used for this purpose. After the lung is collapsed, distal end 12 of shaft 4 is introduced through trocar sleeve 52 and electrode 6 is positioned adjacent internal mammary artery M, by positioning distal end 12 anteriorly and rightward from trocar sleeve 52 under visualization with viewing scope 60. The vacuum source is started so that a continuous vacuum is created through lumen 14 of shaft 4. The surgeon then actuates the electric current by pressing down on foot pedal 44 and gradually dissects mammary artery M free from the surrounding tissues of the inside surface of the chest wall, progressing from near its origin at the subclavian artery towards its bifurcation near the xyphoid process. The spatula shape of electrode 6 facilitates dissection of artery M from the chest wall and allows the surgeon to view distal tip 24 through scope 60.

The smoke generated from cutting the tissues of the inner chest wall around artery M is continuously evacuated through side holes 8. During the procedure, the surgeon may urge electrode 6 into the surrounding tissue until distal end 12 of shaft 4 abuts against this tissue, thereby blocking distal opening 27. Side holes 8, however, are sufficiently proximal of distal end 12 to remain substantially unobstructed during the entire procedure. The surgeon may also exchange vacuum line 52 with an irrigation line in order to deliver fluid through lumen 24 to wash away fluids, tissue or other debris from the site. Bleeding branches of artery M created during the dissection may also be cauterized with electrode 6.

Once the desired segment of artery M has been dissected from the inner thoracic wall, it may be ligated, divided and prepared for anastomosis. After initiating cardiopulmonary bypass and inducing cardioplegic arrest, the free end of the dissected artery M may be sutured to a diseased coronary artery on the heart to bypass an occluded region in the coronary artery. Preferably, the devices and techniques described in commonly assigned patent application Ser. No. 08/282,192, filed Jul. 28, 1994, which is incorporated herein by reference, are utilized to induce cardioplegic arrest and establish cardiopulmonary bypass without performing a median sternotomy. Thoracoscopic techniques for performing an IMA-coronary artery anastomosis are described in U.S. Pat. No. 5,501,698, which has been incorporated herein by reference.

Further embodiments of the electrocautery probe of the invention are illustrated in FIGS. 6–9. In these embodiments, as shown in FIGS. 6A–B, electrocautery probe 102 includes, as in other embodiments, an insulated shaft 104, an electrode tip 106 at the distal end of the shaft, and a handle 108 attached to the proximal end of the shaft. Preferably, shaft 104 includes side holes 110 near its distal end for evacuation of smoke from the surgical area, as described above. A proximal portion 107 of electrode tip 106 is covered with an insulative coating, allowing electrode tip 106 to extend a significant distance distally from the distal end of shaft 104 to facilitate better visibility of the tip and its interaction with tissue, while preventing unintentional burning of tissue due to incidental contact. Electrode tip 106 is preferably angled away from the longitudinal axis of shaft 104 by an angle in a range of about 10 to 60 degrees to facilitate thoracoscopic approaches to the mammary artery via access ports in the anterior or lateral sides of the chest. Electrode tip 106 is preferably 10–15 mm in length from the distal end of shaft 104, and has a transverse width (or diameter) of about 1.5–4.5 mm. Electrode tip 106, shaft 104, and handle 110 may be otherwise designed and constructed similarly to the embodiments described above and shown in FIGS. 1–6.

Handle 108 includes a cutting switch 112 and coagulation switch 114 (for changing the frequency of radiofrequency current delivered to electrode 106, as described above), and an alternating continuous suction/irrigation switch 116. Various embodiments of suction/irrigation switch 116 are illustrated in FIGS. 7–9. In the embodiment of FIGS. 7A–B, suction/irrigation switch 116 comprises a button 118 movably mounted to handle 108 and biased outward by a spring 120. A suction tube 122 and irrigation tube 124 extend through handle 108 and are both connected to the lumen 126 within shaft 104. Suction tube 122 and irrigation tube 124 are made of a soft polymer such as Tygon or silicone with a durometer in the range of 35–70 Shore A. Button 118 has a shaft 128 extending into handle 108 with a foot 130 at its inner end extending transversely to shaft 128 and disposed between suction tube 122 and irrigation tube 124. In switch 116's normally outward position of FIG. 7A, foot 130 pinches irrigation tube 124 closed, blocking flow of irrigation fluid to lumen 126, while vacuum tube 122 remains open, allowing suction to be exerted through lumen 126. When the operator pushes button inward as in FIG. 7B, vacuum tube 122 is pinched closed, stopping vacuum through the lumen 126, while opening irrigation tube 124 to initiate the flow of irrigation fluid through the lumen. In this way, suction is automatically discontinued when irrigation is applied, thereby avoiding the evacuation of irrigation fluid before it has reached the surgical site. Moreover, no materials or moving parts other than tubes 122, 124 contact the irrigation fluid delivered to the surgical site or fluids evacuated from the surgical site, thereby minimizing the deleterious effects of such fluids upon the switch mechanism.

In an alternative embodiment, shown in FIGS. 8A–B, switch 116 again includes a button 118 having a shaft 128 extending into handle 108, with a spring 120 biasing button 118 outward. A rocker arm 132 is pivotably mounted to handle 108 by a first pin 134, and pivotably coupled to shaft 128 by a second pin 136. A first cross-member 138 is mounted transversely to rocker arm 132 on a first end thereof and is disposed between suction tube 122 and irrigation tube 124. A second cross-member 140 is mounted transversely to rocker arm 132 on a second end thereof and is disposed laterally of irrigation tube 124. Opposite second cross-member 140 a stop 142 is mounted to handle 108, irrigation tube 124 extending through a gap between second cross-member 140 and stop 142. In this way, when button 118 is in its normally outward position of FIG. 8A, Irrigation tube 124 is pinched closed, preventing flow of irrigation fluid, while suction tube 122 is open, allowing suction to be applied through lumen 126. When button 118 is depressed as in FIG. 8B, suction tube 122 is pinched closed between second cross-member 140 and stop 142, stopping suction, while opening irrigation tube 124 to allow flow of irrigation fluid through lumen 126.

In a further embodiment, shown in FIGS. 9A–9B, switch 116 again comprises a button 118, shaft 128, and biasing spring 120. In this embodiment, alternation of suction and irrigation does not rely upon pinching off of soft tubes as in previous embodiments. A manifold 144 is attached to the inner end of shaft 128, and includes a Y-shaped fluid pathway with a suction inlet 146, an irrigation fluid inlet 148, and an outlet 150. Manifold 144 is movably mounted within a manifold housing 152. Suction tube 122 is connected to manifold housing 152 at a suction port 154 and irrigation tube 124 is connected to manifold housing 152 at an irrigation port 156. Manifold 144 is movable between an upper position (FIG. 9A) wherein suction inlet 146 is aligned with suction port 154, and a lower position (FIG. 9B) wherein irrigation fluid inlet 148 is aligned with irrigation port 156. In either position, outlet 150 is aligned with an outlet port 168 in manifold housing 152, to which lumen 126 in shaft 104 is fluidly connected by means of an outlet tube 160. In operation, in the normally outward position of FIG. 9A, suction inlet 146 is aligned with suction port 154 allowing suction to be applied through outlet tube 160 and shaft 104. In this position, irrigation fluid inlet 148 is not aligned with irrigation port 156, preventing the flow of irrigation fluid. When button 118 is depressed as in FIG. 9B, irrigation fluid inlet 148 is aligned with irrigation port 156, allowing irrigation fluid to flow through outlet tube 160 and shaft 104, while stopping suction.

While the above is a complete description of the preferred embodiments of the invention, various alternatives, modifications and equivalents may be used. Therefore, the above description should not be taken as limiting the scope of the invention, which is defined by the appended claims.

What is claimed is:

1. A surgical suction and irrigation device comprising:
   a shaft having proximal and distal ends and an inner lumen therebetween, and an opening at the distal end in communication with the inner lumen;
   a handle attached to the proximal end of the shaft;
   an irrigation port on the handle fluidly connected to the inner lumen and adapted for connection to a source of irrigation;
   a suction port on the handle fluidly connected to the inner lumen and adapted for connection to a source of suction; and
   a switch on the handle movable between a first position and a second position, wherein, in the first position, the irrigation port is fluidly isolated from the inner lumen and the suction port is in fluid communication with the inner lumen, and in the second position, the suction port is fluidly isolated from the inner lumen and the irrigation port is in fluid communication with the inner lumen;
   wherein the switch is biased to said first position so that the suction port is in fluid communication with the inner lumen at all times except when the switch is moved to said second position.

2. The device of claim 1 further comprising a first tube connecting the suction port to the inner lumen and a second tube connecting the irrigation port to the inner lumen.

3. The device of claim 2 wherein the first and second tubes are made of a soft polymer with a durometer in a range of 35–70 Shore A.

4. The device of claim 3 wherein the switch is configured to pinch closed the second tube in the first position and to pinch closed the first tube in the second position.

5. The device of claim 4 wherein the switch comprises a button mounted so as to be movable between the first and second positions, the button having an inner end configured to engage the first and second tubes, the inner end pinching closed the second tube in the first position and pinching closed the first tube in the second position.

6. The device of claim 4 wherein the switch comprises a button movably mounted to the handle so as to be movable between the first and second positions, the button having an inner end, and further comprising a rocker arm pivotably mounted to the handle and pivotably coupled to the inner end of the button so as to pivot when the button is moved, the rocker arm having first end for pinching closed the second tube in the first position, and a second end for pinching closed the first tube in the second position.

7. The device of claim 1 wherein the switch comprises a manifold having an inlet and an outlet, the outlet being connected to the inner lumen, the manifold being movable relative to the suction and irrigation ports so as to connect the inlet to the suction port in the first position and to connect the inlet to the irrigation port in the second position.

8. The device of claim 1 wherein the shaft has a plurality of side holes near the distal end in fluid communication with the inner lumen.

9. The device of 1 wherein the distal end of the shaft is configured for introduction through an intercostal space in a patient.

10. The device of claim 9 wherein the distal end of the shaft has a diameter of less than about 10 mm.

11. An electrosurgical device comprising:
a shaft having proximal and distal ends and an inner lumen therebetween, and an opening at the distal end in communication with the inner lumen;
an electrode attached to the distal end of the shaft and extending distally therefrom;
a handle attached to the proximal end of the shaft;
a connector on the handle adapted for connection to a source of electricity;
a conductor for conducting electricity from the connector to the electrode;
an irrigation port on the handle fluidly connected to the inner lumen and adapted for connection to a source of irrigation;
a suction port on the handle fluidly connected to the inner lumen and adapted for connection to a source of suction; and
a switch on the handle movable between a first position and a second position, wherein, in the first position, the irrigation port is fluidly isolated from the inner lumen and the suction port is in fluid communication with the inner lumen, and in the second position, the suction port is fluidly isolated from the inner lumen and the irrigation port is in fluid communication with the inner lumen;
wherein the switch is biased to said first position so that the suction port is in fluid communication with the inner lumen at all times except when the switch is moved to said second position.

12. The device of claim 1 further comprising a first tube connecting the suction port to the inner lumen and a second tube connecting the irrigation port to the inner lumen.

13. The device of claim 12 wherein the first and second tubes are made of a soft polymer with a durometer in a range of 35–70 Shore A.

14. The device of claim 12 wherein the switch is configured to pinch closed the second tube in the first position and to pinch closed the first tube in the second position.

15. The device of claim 14 wherein the switch comprises a button mounted so as to be movable between the first and second positions, the button having an inner end configured to engage the first and second tubes, the inner end pinching closed the second tube in the first position and pinching closed the first tube in the second position.

16. The device of claim 14 wherein the switch comprises a button mounted to the handle so as to be movable between the first and second positions, the button having an inner end, and further comprising a rocker arm pivotably mounted to the handle and pivotably coupled to the inner end of the button so as to pivot when the button is moved, the rocker arm having first end for pinching closed the second tube in the first position, and a second end for pinching closed the first tube in the second position.

17. The device of claim 11 wherein the switch comprises a manifold having an inlet and an outlet, the outlet being connected to the inner lumen, the manifold being movable relative to the suction and irrigation ports so as to connect the inlet to the suction port in the first position and to connect the inlet to the irrigation port in the second position.

18. The device of claim 11 further comprising an electrical switch on the handle for selectively connecting the connector to the electrode.

19. The device of claim 11 wherein the conductor comprises a conductive portion of the shaft.

20. The device of claim 11 wherein the shaft has a plurality of side holes near the distal end in fluid communication with the inner lumen.

21. The device of claim 20 wherein the shaft is conductive and the side holes have side walls covered by an insulative material.

22. The device of 1 wherein the distal end of the shaft is configured for introduction through an intercostal space in a patient.

23. The device of claim 22 wherein the distal end of the shaft has a diameter of less than about 10 mm.

24. The device of claim 11 wherein the electrode comprises a conductive extension portion having a proximal end attached to the shaft and a distal end;
an insulative covering over the extension portion; and
a conductive paddle attached to the distal end of the extension portion.

25. The device of claim 11 wherein the electrode is at least about 10 mm in length from the distal end of the shaft.

26. A method for electrically cauterizing tissue comprising the steps of:
providing an electrocautery device having a shaft with a distal end, a proximal end, an electrode at the distal end, an inner lumen, and an opening at the distal end in communication with the inner lumen;
connecting the inner lumen of the shaft to an irrigation source;
connecting the inner lumen of the shaft to a source of suction;
conducting electricity to the electrode;
cauterizing the tissue with the electrode;
continuously applying suction during the cauterizing step to evacuate smoke through the inner lumen; and
moving a switch on the electrocautery device from a first position to a second position so as to cause irrigation fluid to flow through the inner lumen, the suction being automatically discontinued when the switch is in the second position, and automatically continued as soon as the switch moves from the second position to the first position.

27. The method of claim 26 wherein the actuating step comprises moving the switch to engage a tube connecting a source of suction to the inner lumen, the tube being pinched closed in the second position.

28. The method of claim 27 wherein, in the first position, the switch is engaging a second tube connecting a source of irrigation fluid to the inner lumen, the second tube being pinched closed in the first position.

* * * * *